United States Patent [19]

Durant et al.

[11] 4,027,026

[45] May 31, 1977

[54] PHARMACEUTICAL COMPOSITIONS AND METHODS OF INHIBITING H-2 HISTAMINE RECEPTORS WITH PYRIDYL SUBSTITUTED THIOALKYL- AND OXYALKYL-THIOUREAS AND UREAS

[75] Inventors: Graham John Durant, Welwyn Garden City; John Colin Emmett, Codicote; Charon Robin Ganellin, Welwyn Garden City, all of England

[73] Assignee: Smith Kline & French Laboratories Limited, Welwyn Garden City, England

[22] Filed: June 13, 1975

[21] Appl. No.: 586,670

Related U.S. Application Data

[60] Division of Ser. No. 450,937, March 13, 1974, Pat. No. 3,905,984, which is a continuation-in-part of Ser. No. 290,584, Sept. 20, 1972, abandoned, which is a continuation-in-part of Ser. No. 230,451, Feb. 29, 1972, abandoned.

[30] Foreign Application Priority Data

| Mar. 9, 1971 | United Kingdom | 6352/71 |
| July 22, 1971 | United Kingdom | 34334/71 |
| Feb. 3, 1972 | Ireland | 136/72 |

[52] U.S. Cl. .................................. 424/263
[51] Int. Cl.$^2$ .............................. A61K 31/44
[58] Field of Search ............................ 424/263

[56] References Cited

UNITED STATES PATENTS

| 3,535,328 | 10/1970 | Zielinski | 424/263 |
| 3,590,029 | 6/1971 | Koch et al. | 260/211.5 R |
| 3,736,331 | 5/1973 | Black et al. | 424/263 |
| 3,759,944 | 9/1973 | Black et al. | 424/266 |

*Primary Examiner*—Albert T. Meyers
*Assistant Examiner*—Daren M. Stephens
*Attorney, Agent, or Firm*—Joan S. Keps; Richard D. Foggio; William H. Edgerton

[57] ABSTRACT

Pharmaceutical compositions and methods of inhibiting H-2 histamine receptors with pyridyl substituted thioalkyl- and oxyalkyl-thioureas and ureas.

13 Claims, No Drawings

PHARMACEUTICAL COMPOSITIONS AND METHODS OF INHIBITING H-2 HISTAMINE RECEPTORS WITH PYRIDYL SUBSTITUTED THIOALKYL- AND OXYALKYL-THIOUREAS AND UREAS

This application is a division of application Ser. No. 450,937 filed Mar. 13, 1974, now U.S. Pat. No. 3,905,984, which is a continuation-in-part of Ser. No. 290,584 filed Sept. 20, 1972, now abandoned, which is a continuation-in-part of Ser. No. 230,451 filed Feb. 29, 1972, now abandoned.

This invention relates to pharmacologically active compounds, to pharmaceutical compositions and to methods of inhibiting H-2 histamine receptors. The compounds of the invention can exist as the addition salts but, for convenience, reference will be made throughout this specification to the parent compounds.

It has for long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated by Ash & Schild (Brit. J. Pharmac. 1966, 27, 427) as H-1. The substances of the present invention are distinguished by the fact that they act at histamine H-2 receptors which, as described by Black et al. (Nature, 1972, 236, 385), are histamine receptors other than the H-1 receptor. Thus they are of utility in inhibiting certain actions of histamine which are not inhibited by the above-mentioned "antihistamines". Black et al., cited above, page 390, column 2, state the following: "Mepyramine has been defined as an $H_1$-receptor antagonist[1] and burimamide has now been defined as an $H_2$-receptor antagonist. Used alone, burimamide can antagonize those responses to histamine, such as stimulation of acid gastric secretion, which cannot be blocked by mepyramine; histamine apparently activates $H_2$-receptors to produce these effects." Thus, from the Black et al. paper, H-2 histamine receptors are those histamine receptors which are not inhibited by mepyramine but are inhibited by burimamide. The substances of this invention may also be of utility as inhibitors of certain actions of gastrin.

The compounds with which the present invention is concerned may be represented by the following general formula; insofar as tautomerism affects the compounds mentioned in this specification, the numbering of the nucleus has been modified accordingly;

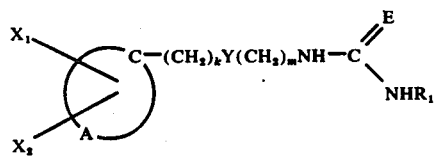

FORMULA I wherein A is such that there is formed together with the carbon atom shown a pyridine ring; $X_1$ is hydrogen, lower alkyl, hydroxyl, trifluoromethyl, halogen, amino or

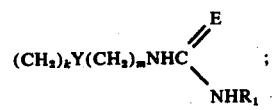

$X_2$ is hydrogen or when $X_1$ is lower alkyl, lower alkyl or halogen; $k$ is 1 or 2 and $m$ is 2 or 3, provided that the sum of $k$ and $m$ is 3 or 4; Y is oxygen or sulphur; E is oxygen or sulphur; and $R_1$ is hydrogen, lower alkyl, benzoyl or di-lower alkylamino-lower alkyl or a pharmaceutically acceptable addition salt thereof. Preferably A is such that the nitrogen atom is adjacent to the carbon atom shown. Preferably $X_1$ is hydrogen, methyl, bromo, amino or hydroxyl and $X_2$ is hydrogen. One group of preferred compounds within the present invention is that wherein Y and E are sulphur, $k$ is 1, $m$ is 2 and $R_1$ is methyl. Preferred compounds of this invention are N-methyl-N'-[2-((3-hydroxy-2-pyridyl)methylthio)ethyl]thiourea and N-methyl-N'-[2-((3-bromo-2-pyridyl)methylthio)ethyl]thiourea.

The pharmaceutical compositions of this invention comprise a pharmaceutical carrier and, as the active ingredient, a compound of Formula I, in which $k$ is 0 to 2 and the other terms are as defined therein, or a pharmaceutically acceptable acid addition salt thereof.

The methods of inhibiting H-2 histamine receptors in accordance with this invention comprise administering to an animal a compound which is an active ingredient of the pharmaceutical compositions of this invention.

The compounds with which the present invention is concerned wherein Y is sulphur and $k$ is 1 or 2 may be produced by processes which commence with a substance of the following general formula:

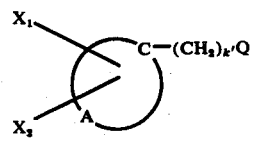

FORMULA II wherein A, $X_1$ and $X_2$ have the same significance as in Formula I except that $X_1$ may not be

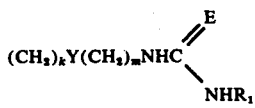

but may additionally be $(CH_2)_{k'}Q$; $k'$ is 1 or 2 and Q is hydroxyl, halogen or methoxy. In the first stage of these processes, the compound of Formula II is reacted with an amino-mercaptan of the following FORMULA III:

FORMULA III wherein $m$ has the same significance as in Formula I. When Q is halogen, this reaction may be carried out under strongly basic conditions, for example in the presence of sodium ethoxide or sodium hydroxide. Since the substance of Formula III is a primary amine it may be necessary to protect the amino group, for example by a phthalimido group which may subsequently be removed by acid hydrolysis or by hydrazinolysis.

When Q is hydroxyl or halogen it is found that the reaction will take place under acidic conditions e.g. in the presence of a halogen acid such as 48% aqueous hydrogen bromide, or a halogen acid in the presence of glacial acetic acid. When Q is methoxy, the reaction will also take place in the presence of 48% hydrogen bromide.

When $k$ is zero, the corresponding first stage of the reaction is between a nucleus directly substituted with a thiol or a thione and, under acidic conditions, 3-aminopropanol or, under alkaline conditions, a 3-halopropylamine, the amino group being protected if required in the latter case, e.g., by a phthalimido group which may subsequently be removed by acid hydrolysis.

The product produced by these processes is of the following formula IV, and may, of course, be in the form of the acid addition salt.

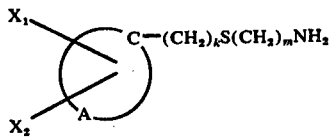

FORMULA IV wherein $X_1$ has the same significance as in formula II and A, $X_2$, $k$ and $m$ have the same significance as in formula I. The free base of formula IV may be obtained from the acid addition salt by treatment with an appropriate base, e.g., an alkali metal alkoxide such as sodium ethoxide or an inorganic base such as potassium carbonate.

The compounds of formula I, where $R_1$ is hydrogen, Y is sulphur and E is sulphur may be prepared from an amine of formula IV be reaction with an acyl isothiocyanate such as benzoyl isothiocyanate in an appropriate solvent such as chloroform. Alkaline hydrolysis of these compounds, e.g., the benzoyl derivatives where $R_1$ is $C_6H_5CO$, with a reagent such as aqueous potassium hydroxide or aqueous potassium carbonate yields the compounds of formula I where $R_1$ is hydrogen and Y and E are sulphur.

Compounds of formula I wherein $R_1$ is hydrogen, Y is sulphur and E is sulphur may alternatively be prepared directly from the amine of formula IV by reaction at elevated temperature with the thiocyanate of ammonium or of a metal such as sodium or potassium.

The compounds of formula I where $R_1$ is lower alkyl or dialkylaminoalkyl, Y is sulphur and E is sulphur may be prepared from the amine of formula IV by reaction with an isothiocyanic ester of formula $R_1-N=C=S$ in an appropriate solvent such as chloroform, ethanol, isopropanol, acetonitrile or water.

Alternatively the amine of formula IV may be converted by reaction with carbon disulphide to the dithiocarbamic acid of the formula:

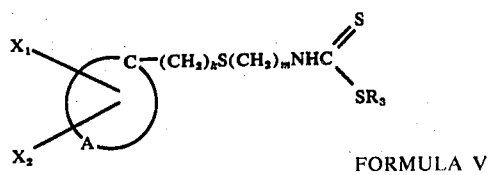

FORMULA V wherein, A, $X_1$, $X_2$, $k$ and $m$ have the same significance as in formula IV and $R_3$ is hydrogen and then methylated to yield the compound of formula V wherein $R_3$ is methyl. Finally, reaction of this methyl ester with an amine of formula $R_1NH_2$, wherein $R_1$ is lower alkyl, yields the required compound.

In the case of compounds of formula I wherein Y is oxygen, the process for their production commences with a compound of formula VI (which may itself be formed by treatment with thionyl halide of the corresponding alcohol resulting from the reaction of a haloalkyl heterocyclic compound and the sodium salt of a diol)

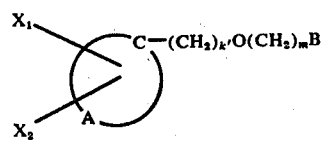

FORMULA VI wherein A, $X_1$, $X_2$ and $m$ have the same significance as in formula I, $k'$ is 1 or 2, $k' + m$ is 3 or 4 and B is halogen. This compound may be reacted with an alkali metal azide and the resulting product reduced, e.g., by hydrogenation over a platinum dioxide catalyst to yield an amine of formula VII in which $k$ is 1 or 2.

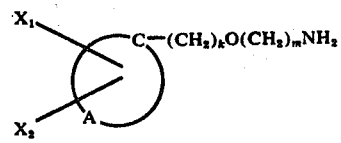

FORMULA VII and wherein A, $X_1$, $X_2$ and $m$ have the same significance as in formula I.

The amines of formula VII in which $k$ is zero are prepared by reacting a halo-pyridine under strongly basic conditions with propylene glycol and converting the resultant 3-hydroxypropoxy compound with thionyl chloride to the corresponding 3-chloropropoxy compound which on reaction with sodium azide and reduction of the product yields the required amine.

The compounds of formula VII may be converted to the compounds of formula I wherein Y is oxygen and E is sulphur by methods analogous to those described hereinabove for the conversion of the compounds of formula IV to those of formula I wherein both Y and E are sulphur.

Compounds of formula I wherein E is oxygen may be formed from the amines of formula IV or formula VII by treatment thereof with an isocyanate of formula $R_1NCO$ wherein $R_1$ is lower alkyl, benzoyl or dialkylaminoalkyl. The compounds of formula I wherein E is oxygen and $R_1$ is hydrogen may be obtained by reaction of the said amines with sodium or potassium cyanate.

As stated above, the compounds represented by formula I have been found to have pharmacological activity in the animal body as antagonists to certain actions of histamine which are not blocked by "antihistamines" such as mepyramine. For example, they have been found to inhibit selectively the histamine-stimulated secretion of gastric acid from the perfused stomachs of rats anaesthetised with urethane, at doses from 0.5 to 256 micromoles per kilogram intravenously. Similarly, the action of these compounds is demonstrated by their antagonism to the effects of histamine on other tissues which, according to the above mentioned paper of Ash & Schild, are not H-1 receptors. Examples of such tissues are perfused isolated guinea-pig heart, isolated guinea-pig right atrium and isolated rat uterus. The compounds of the invention have also been found to inhibit the secretion of gastric acid stimulated by pentagastrin or by food. In addition to the above the compounds of the invention also show anti-inflammatory activity in conventional tests such as the rat paw oedema test at doses of about 500 micromoles/kg. subcutaneously.

The level of activity found for the compositions comprising the compounds of the present invention is illustrated by the effective dose range in the anaesthetised rat, as mentioned above of from 0.5 to 256 micromoles per kilogram, given intravenously, and also by the dose effective in the rat paw oedema test.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg. to about 250 mg., most preferably from about 100 mg. to about 200 mg.

The active ingredient will preferably be administered in equal doses one to three times per day. The daily dosage regimen will preferably be from about 150 mg. to about 750 mg., most preferably from about 300 mg. to about 600 mg.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, picric and maleic acids.

Other pharmacologically active compounds may in certain cases be included in the composition. Advantageously the composition will be made up in a dosage unit form appropriate to the desired mode of administration, for example as a tablet, capsule, injectable solution or, when used as an anti-inflammatory agent, as a cream for topical administration.

The invention is illustrated but in no way limited by the following examples:

EXAMPLE 1

N-Methyl-N'-[2-(2-pyridylmethylthio)ethyl]thiourea i. a. A solution of 2-hydroxymethyl pyridine (5.45 g.) and cysteamine hydrochloride (6.2 g.) in aqueous hydrobromic acid (110 ml., 48%) was heated under reflux overnight. After cooling, the solution was evaporated to dryness and the residual solid washed with ethanol/ether and recrystallised from aqueous ethanol to give 2-[(2-aminoethyl)thiomethyl]pyridine dihydrobromide m.p. 191°–193°.

b. Phthalimidoethanethiol (2 g.) was added portionwise with stirring to a solution of sodium ethoxide (prepared from 0.23 g. of sodium) in ethanol (20 ml.) at 0° under a nitrogen atmosphere. After stirring at 0° for a further 2½ hours, the resulting yellow solution was cooled with an ice-salt bath and a solution of 2-chloromethylpyridine hydrochloride (0.83 g.) in ethanol (5 ml.) was added dropwise over 10 minutes. After addition the mixture was stirred at room temperature overnight, then acidified with ethanolic hydrogen chloride and evaporated to dryness. Addition of water precipitated unreacted phthalimidoethanethiol which was removed by filtration. The filtrate was concentrated and basified with aqueous sodium bicarbonate solution to give 2-[(2-phthalimodoethyl)thiomethyl]pyridine. A stirred mixture of this phthalimido derivative (0.65 g.) in aqueous hydrobromic acid (40 ml. 18%) was heated under reflux overnight. After cooling to 0°, the resulting clear solution was filtered and the filtrate evaporated to dryness. Recrystallisation of the residue from aqueous ethanol gave 2-[(2-aminoethyl)-thiomethyl]pyridine dihydrobromide (0.55 g.), m.p. 191°–193°.

c. A suspension of cysteamine hydrochloride (118.8 g.) in ethanol (200 ml., dried over molecular sieves) was added portionwise at 0° to a solution of sodium ethoxide (prepared from 48 g. of sodium) in ethanol (1 liter) under a nitrogen atmosphere. After stirring at 0°, for a further 2 hours, a solution of 2-chloromethylpyridine hydrochloride (78 g.) in ethanol (400 ml.) was added dropwise over 45 minutes while the temperature was maintained at −1°±2°. After addition, the mixture was stirred at room temperature overnight, filtered, and the filtrate acidified with concentrated hydrochloric acid. The solution was then evaporated to dryness, the residue dissolved in ethanol (1 liter) and a solution of excess picric acid in hot ethanol added. The resulting crude picrate was dissolved in water (2.7 liters) and, after decantation from an insoluble oil, the solution was left to cool to give 2-((2-aminoethyl)thiomethyl)pyridine dipicrate.

Treatment of this picrate with aqueous hydrobromic acid followed by extraction with toluene gave the dihydrobromide, m.p. 191°–193°, after evaporation to dryness and recrystallisation of the crude residue from ethanol.

ii. an aqueous solution of 2-((aminoethyl)thiomethyl)pyridine dihydrobromide (4.95 g.) was basified with excess solid potassium carbonate. The resultant paste was extracted with ether/ethanol (1:1) and the extracts dried and evaporated, leaving a residual amine (2.45 g.) which was dissolved in ethanol and a solution of methyl isothiocyanate (1.21 g.) in isopropyl alcohol (4 ml.) added. The reaction mixture was then heated under reflux for 1 hour and, after cooling, evaporated to dryness. The residual oil was chromatographed on a column of silica gel with ethyl acetate as eluant to give N-methyl-N'-[2-(2-pyridylmethylthio)ethyl]thiourea (2.4 g.) as a clear oil. (Found: C, 49.4; H, 6.3; N, 17.3; S, 26.2; $C_{10}H_{15}N_3S_2$ requires: C, 49.8; H, 6.3; N, 17.4; S, 26.6.)

EXAMPLES 2–8

By two-stage processes essentially similar to those described in Example 1(i) and (ii) were produced thiourea compounds of the formula:

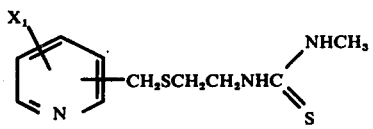

wherein $X_1$ and the position of attachment of the side chain are as set out in the following Table 1.

ric acid, thus yielding the corresponding hydrochloride or hydrobromide, as described in Example 1 (i)(c).

Conversion of this hydrochloride or hydrobromide into the free base by the addition of potassium carbonate followed by concentration and extraction with isopropanol or ether/ethanol (3:1) yielded an extract which was reacted with methyl isothiocyanate in an appropriate solvent under conditions similar to those described in example 1 (ii). The resultant thiourea products, where crystallisable, were recrystallised from a solvent as indicated in table 1.

EXAMPLE 9

N-Methyl-N'-[3-(2-pyridylthio)propyl]thiourea i. A solution of 2-mercaptopyridine (2.2 g.) and 3-aminopropanol (1.14 ml.) in hydrobromic acid (48%, 25 ml.) was heated under reflux for 25 hours. The reaction mixture was evaporated to dryness and the oily residual solid recrystallised twice from ethanol to give 2-(3-aminopropylmercapto)pyridine dihydrobromide (3.2 g.) m.p. 186°–188°.

ii. This amine dihydrobromide (7 g.) was converted to the free base and reacted with methyl isothiocyanate (1.60 g.) in ethanol to give a crude yellow solid after

TABLE I

| Ex. No. | $X_1$ | Posn. attach. of side chain | Interm amine salt m.p. (°C) | Recryst. from | m.p. (° C) | Product: N-methyl-N'-[2-(* * *)methylthio)ethyl]thiourea Molecular Formula | Elemental Analysis | | | | | | | * * * |
|---|---|---|---|---|---|---|---|---|---|---|---|---|---|---|
| | | | | | | | Found | | | | Required | | | |
| | | | | | | | C | H | N | S | C | H | N | S | |
| 2 | 3-$CH_3$ | 2 | 171-3 | — | — | $C_{11}H_{17}N_3S_2$ | 51.4 | 6.5 | 16.2 | 24.8 | 51.7 | 6.7 | 16.5 | 25.1 | 3-methyl-2-pyridyl |
| 3 | 6-$CH_3$ | 2 | 188-9 | isopropyl acetate | 82-83 | $C_{11}H_{17}N_3S_2$ | 51.8 | 7.0 | 16.6 | 21.6 | 51.7 | 6.7 | 16.5 | 25.1 | 6-methyl-2-pyridyl |
| 4 | H | 3 | 185-7 | methanol-ether | 78-80 | $C_{10}H_{15}N_3S_2$ | 49.5 | 6.2 | 17.3 | 26.5 | 49.8 | 6.3 | 17.4 | 26.6 | 3-pyridyl |
| 5 | H | 4 | 236-8 | — | — | $C_{10}H_{15}N_3S_2$ | 49.9 | 6.5 | 17.3 | 26.3 | 49.8 | 6.3 | 17.4 | 26.6 | 4-pyridyl |
| 6 | 3-OH | 2 | 231-2 | water | 130-133 | $C_{10}H_{15}N_3OS_2$ | 46.4 | 5.9 | 16.1 | 24.8 | 46.7 | 5.9 | 16.3 | 24.9 | 3-hydroxy-2-pyridyl |
| 7 | 3-Br | 2 | 252-4 | — | low m.p. solid | $C_{10}H_{14}BrN_3S_2$ | 37.1 | 4.7 | 13.2 | 19.9 | 37.5 | 4.4 | 13.1 | 20.0 | 3-bromo-2-pyridyl |
| 8 | 5-OH | 2 | 210-2 | water | 130-2 | $C_{10}H_{15}N_3OS_2$ | 46.9 | 5.7 | 16.5 | 24.9 | 46.7 | 5.9 | 16.3 | 24.9 | 5-hydroxy-2-pyridyl |

The solvent from which the product was crystallised and the melting point and elemental analysis data of the product are also set out in the table together with the melting point of the corresponding intermediate amine salt of the formula:

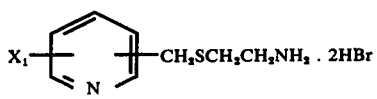

The starting materials of formula:

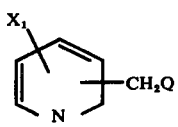

wherein Q is hydroxyl, halogen or methoxy are all known compounds. In each case, the starting material was reacted with cysteamine hydrochloride in aqueous hydrobromic acid as described in Example 1 (i) a. Where necessary, the resultant amine was purified by conversion to the picrate followed by treatment with hydrochloric or hydrobromic acid and removal of picevaporation of the reaction mixture. This crude product was chromatographed on silica gel with elution by methanol-ethyl acetate (1:3), treated with aqueous hydrochloric acid, concentrated and recrystallised from ethanol/ether to give N-methyl-N'-[3-(2-pyridylthio)propyl]thiourea hydrochloride m.p. 140°–142°.

(Found: C, 43.4; H, 6.0; N, 15.1; S, 23.0; Cl, 12.7 $C_{10}H_{15}N_3S_2$.HCl, requires: C, 43.2; H, 5.8; N, 15.1; S, 23.1; Cl, 12.8)

EXAMPLE 10

N-Methyl-N'-[2-(2-pyridylmethylthio)ethyl]urea

A mixture of 2-[(2-aminoethyl)thiomethyl]pyridine (7.0 g.) and methyl isocyanate (2.7 g.) in acetonitrile was heated for 18 hours in a pressure vessel at 100°. After cooling, the solid obtained was collected and recrystallised from acetonitrile/ether to give N-methyl-N'-[2-(2-pyridylmethylthio)ethyl]urea m.p. 63°–66°.

EXAMPLE 11

N-Methyl-N'-[2-((3-amino-2-pyridyl)methylthio)ethyl]thiourea i. Lithium aluminium hydride (3.2 g.) was added in portions to a solution of ethyl-3-aminopicolinate (6.8 g.) in dry ether (150 ml.) under nitrogen with stirring and cooling. After addition, the suspension was heated under reflux for 30 minutes and diluted with ether (150 ml.) then cooled during the addition of water (3.2 ml.) dilute sodium hydroxide (3.2 ml.) and water (9.6 ml.). The slurry was stirred at room temperature for 30 minutes, magnesium sulphate was added and the whole filtered, the residue being washed well with ether. Concentration followed by treatment of the residue with hydrogen chloride in ether gave 3-amino-2-hydroxymethylpyridine hydrochloride (4.2 g.) m.p. 292°-300°. which was recrystallised from methanol-ether without change in melting point.

ii. A solution of 3-amino-2-hydroxymethylpyridine hydrochloride (3.4 g.) and cysteamine hydrochloride (2.38 g.) in aqueous hydrobromic acid (50 ml. 48%) was heated under reflux for 12 hours. Concentration under reduced pressure followed by re-evaporation of the residue with ethanol gave a yellow solid (7.5 g.) which was recrystallised from methanol-ether to afford 3-amino-2-[(2-aminoethyl)thiomethyl]pyridine dihydrobromide (5.8 g.) m.p. 195°-196°.

iii. 3-Amino-2-[(2-aminoethyl)thiomethyl]pyridine (3.0 g,) prepared from an aqueous slurry of the dihydrobromide and potassium carbonate, by extraction with ethanol-ether (2:1) was dissolved in ethanol (25 ml.), methyl isothiocyanate (1.16 g.) added, and the solution then heated under reflux for 30 minutes. The residue was triturated with ether affording a solid (3.4 g.) m.p. 98°-100°. Recrystallisation from isopropyl acetate gave N-methyl-N'-[2-((3-amino-2-pyridyl)methylthio)ethyl]thiourea in 3 crops, m.p. 99.5°-100.5 (1.33 g.), m.p. 100°-101° (1.04 g.) and m.p. 99°-100° (1.0 g.).

(Found: C, 47.2; H, 6.3; N, 21.7; S, 24.4 $C_{10}H_{16}N_4S_2$ requires: C, 46.8; H, 6.3; N, 21.9; S, 25.0)

EXAMPLE 12

In the procedure of Example 1, using in place of 2-hydroxymethylpyridine the following compounds:
2-hydroxymethyl-5-trifluoromethylpyridine
2,4-dihydroxymethyl)pyridine
2-hydroxymethyl-4,6-dimethylpyridine
4-chloro-2-hydroxymethyl-6-methylpyridine
the products are, respectively:
N-methyl-N'-[2-((5-trifluoromethyl-2-pyridyl)methylthio)ethyl]thiourea
2,4-bis[2-(N-methylthioureido)ethylthiomethyl]pyridine.
N-methyl-N'-[2-((4,6-dimethyl-2-pyridyl)methylthio)ethyl]thiourea
N-methyl-N'-[2-((4-chloro-6-methyl-2-pyridyl)methylthio)ethyl]thiourea

EXAMPLE 13

N-Metyl-N'-[2-(2-pyridylmethoxy)ethyl]thiourea

2-Chloromethylpyridine is reacted with the sodium salt of ethylene glycol to give 2-(2-hydroxyethoxymethylpyridine. Treatment of 2-(2-hydroxyethoxymethyl)pyridine with thionyl chloride gives 2-(2-chloroethoxymethyl)pyridine.

A stirred suspension of 2-(2-chloroethoxymethyl)pyridine hydrochloride and sodium azide (9.8 g.) in dry dimethylformamide (103 ml.) is maintained at 95° for 5 hours and then set aside overnight at room temperature. Following dilution with water and filtration, the filtrate is concentrated and the residue purified by chromatography on a dry column of alumina using ethanol. The product is basified with potassium carbonate (6.5 g.) in water (3 ml.) and the anhydrous residue is extracted with isopropyl alcohol (3 × 50 ml.). Concentration of the extracts gives 2-(2-azidoethoxymetyl)pyridine. Hydrogenation of the azido compound in isopropyl alcohol over platinum oxide catalyst gives 2-(2-aminoethoxymethyl)pyridine.

2-(2-Aminoethoxymethyl)pyridine is caused to react with methyl isothiocyanate (1.21 g.) in isopropyl alcohol (25 ml.) by the procedure of Example 1 to give N-methyl-N'-[2-(2-pyridylmethoxy)ethyl]-thiourea.

EXAMPLE 14

N-Methyl-N'-[2-(2-(2-pyridyl)ethyl)thioethyl]thiourea

Using 2-chloroethylpyridine hydrochloride in place of 2-chloromethylpyridine hydrochloride in the procedure of Example 1 (i) (c) gives 2-((2-aminoethyl)thioethyl)-pyridine dihydrobromide. Reacting this intermediate with methyl isothiocyanate by the procedure of Example 1 gives the title compound.

EXAMPLE 15

N-(2-Dimethylaminoethyl)-N'-[2-(2-pyridylmethylthio)-ethyl]thiourea

Treatment of 2-[(2-aminoethyl)thiomethyl]pyridine with 2-dimethylaminoethyl isothiocyanate by the procedure of Example 1 gives the title compound.

EXAMPLE 16

N-[2-(2-Pyridylmethylthio)ethyl]thiourea

A solution of 2-[(2-aminoethyl)thiomethyl]pyridine (6.0 g.) and benzoyl isothiocyanate (6.0 g.) in chloroform (150 ml.) is heated under reflux for one hour and concentrated to give N-benzoyl-N'-[2-(2-pyridylmethylthio)ethyl]thiourea.

The benzoyl thiourea is added to a solution of potassium carbonate (1.4 g.) in water (80 ml.) at 60°. The solution is maintained at this temperature for one hour, concentrated to low bulk and acidified with hydrochloric acid. Benzoic acid is removed by filtration and the filtrate is basified with potassium carbonate and concentrated under reduced pressure. Following extraction with isopropyl alcohol and concentration, the product is N-[2-(2-pyridylmethylthio)ethyl]thiourea.

EXAMPLE 17

Treatment of N-methyl-N'-[2-((2-pyridyl)methylthio)ethyl]thiourea with aqueous hydrobromic acid gives the hydrobromide salt.

Also, treatment of N-methyl-N'-[2-((2-pyridyl)methylthio)-ethyl]thiourea with picric acid in ethanol gives the picrate salt.

EXAMPLE 18

| Ingredients | Amounts |
| --- | --- |
| N-Methyl-N'-[2-((3-hydroxy-2-pyridyl)-methylthic)ethyl]thiourea | 150 mg. |
| Sucrose | 75 mg. |
| Starch | 25 mg. |
| Talc | 5 mg. |
| Stearic acid | 2 mg. |

The ingredients are screened, mixed and filled into a hard gelatin capsule.

EXAMPLE 19

| Ingredients | Amounts |
| --- | --- |
| N-Methyl-N'-[2-((3-bromo-2-pyridyl)-methylthio)ethyl]thiourea | 200 mg. |
| Lactose | 100 mg. |

The ingredients are screened, mixed and filled into a hard gelatin capsule.

The pharmaceutical compositions prepared as in Example 18 and 19 are administered to a subject within the dose ranges given hereabove to inhibit H-2 histamine receptors.

What we claim is:

1. A pharmaceutical composition to inhibit H-2 histamine receptors, said H-2 histamine receptors being those histamine receptors which are not inhibited by mepyramine but are inhibited by burimamide, comprising a pharmaceutical carrier and in an effective amount to inhibit said receptors a pyridyl compound of the formula:

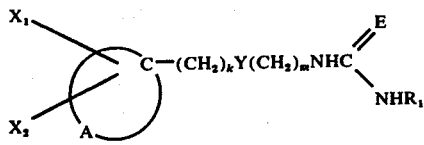

wherein A is such that there is formed together with the carbon atom show a pyridine ring; $X_1$ is hydrogen, lower alkyl, hydroxyl, trifluoromethyl, halogen, amino or

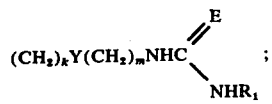

$X_2$ is hydrogen or, when $X_1$ is lower alkyl, lower alkyl or halogen; $k$ is 0 to 2 and $m$ is 2 or 3, provided that the sum of $k$ and $m$ is 3 or 4; Y is oxygen or sulphur; E is oxygen or sulphur; $R_1$ is hydrogen, lower alkyl, benzoyl or di-lower alkylamino- lower alkyl, or a pharmaceutically acceptable addition salt thereof.

2. A pharmaceutical composition of claim 1 in which the pyridyl compound is N-methyl-N'-[3-(2-pyridylthio)-propyl]-thiourea.

3. A pharmaceutical composition of claim 1 wherein k is 1 and m is 2.

4. A pharmaceutical composition of claim 1 in which $X_1$ is hydrogen, methyl, bromo, hydroxyl or amino and $X_2$ is hydrogen; Y and E are sulphur and $R_1$ is methyl.

5. A pharmaceutical composition of claim 1 in which the pyridyl compound is N-methyl-N'-[2-((3-hydroxy-2-pyridyl)methylthio)ethyl]thiourea.

6. A pharmaceutical composition of claim 1 in which the pyridyl compound is N-methyl-N'-[2-((3-bromo-2-pyridyl)methylthio)ethyl]thiourea.

7. A pharmaceutical composition of claim 1 in which the pyridyl compond is present in an amount of from about 50 mg. to about 250 mg.

8. A method of inhibiting H-2 histamine receptors, said H-2 histamine receptors being those histamine receptors which are not inhibited by mepyramine but are inhibited by burimamide, which comprises administering to an animal in need of inhibition of said receptors in an effective amount to inhibit said receptors a pyridyl compound of the formula:

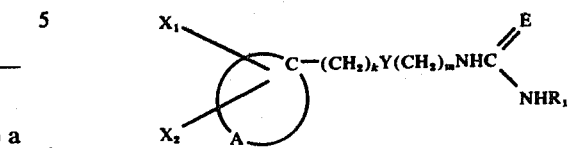

wherein A is such that there is formed together with the carbon atom shown a pyridine ring; $X_1$ is hydrogen, lower alkyl, hydroxyl, trifluoromethyl, halogen, amino or

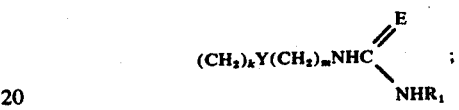

$X_2$ is hydrogen or, when $X_1$ is lower alkyl, lower alkyl or halogen; $k$ is 0 to 2 and $m$ is 2 or 3, provided that the sum of $k$ and $m$ is 3 or 4; Y is oxygen or sulphur; E is oxygen or sulphur; $R_1$ is hydrogen, lower alkyl, benzoyl or di-lower alkylamino-lower alkyl, or a pharmaceutically acceptable addition salt thereof.

9. A method of claim 8 in which the pyridyl compound is N-methyl-N'-[3-(2-pyridylthio)propyl]thiourea.

10. A method of claim 8 in which the pyridyl compound is N-methyl-N'-[2-((3-hydroxy-2-pyridyl)methylthio)-ethyl]thiourea.

11. A method of claim 8 in which the pyridyl compound is N-methyl-N'-[2-((3-bromo-2-pyridyl)methylthio)ethyl]thiourea.

12. A method of claim 8 in which the pyridyl compound is administered in a daily dosage of from about 150 mg. to about 750 mg.

13. A method of inhibiting gastric acid secretion which comprises administering internally to an animal in need of inhibition of gastric acid secretion in an effective amount to inhibit gastric acid secretion a pyridyl compound of the formula:

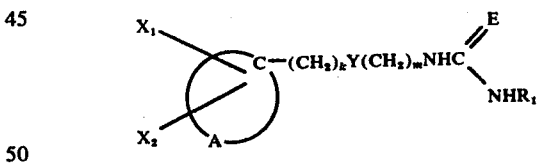

wherein A is such that there is formed together with the carbon atom shown a pyridine ring; $X_1$ is hydrogen, lower alkyl, hydroxyl, trifluoromethyl, halogen, amino or

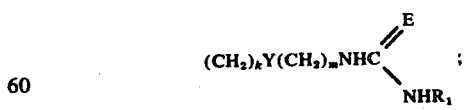

$X_2$ is hydrogen or, when $X_1$ is lower alkyl, lower alkyl or halogen; $k$ is 0 to 2 and $m$ is 2 or 3, provided that the sum of $k$ and $m$ is 3 or 4; Y is oxygen or sulphur; E is oxygen or sulphur; $R_1$ is hydrogen, lower alkyl, benzoyl or di-lower alkylamino-lower alkyl, or a pharmaceutically acceptable addition salt thereof.

* * * * *